(12) United States Patent
Dennewald

(10) Patent No.: US 11,219,322 B2
(45) Date of Patent: Jan. 11, 2022

(54) CAVITY CONTOUR PILLOW

(71) Applicant: DENNEROLL HOLDINGS PTY LTD, Cromer (AU)

(72) Inventor: Adrian Dennewald, Waverton (AU)

(73) Assignee: DENNEROLL HOLDINGS PTY LTD, Cromer (AU)

( * ) Notice: Subject to any disclaimer, the term of this patent is extended or adjusted under 35 U.S.C. 154(b) by 17 days.

(21) Appl. No.: 16/581,726

(22) Filed: Sep. 24, 2019

(65) Prior Publication Data

US 2020/0093297 A1    Mar. 26, 2020

Related U.S. Application Data

(60) Provisional application No. 62/735,195, filed on Sep. 24, 2018.

(51) Int. Cl.
| | | |
|---|---|---|
| *A47G 9/10* | (2006.01) | |
| *A61F 5/37* | (2006.01) | |
| *A61F 5/055* | (2006.01) | |

(52) U.S. Cl.
CPC ............. *A47G 9/1081* (2013.01); *A47G 9/10* (2013.01); *A61F 5/055* (2013.01); *A61F 5/3707* (2013.01)

(58) Field of Classification Search
CPC ...... A47G 9/1081; A47G 9/1009; A47G 9/10; A61F 5/055; A61F 5/3707
See application file for complete search history.

(56) References Cited

U.S. PATENT DOCUMENTS

| | | |
|---|---|---|
| 2,700,779 A | 2/1955 | Tolkowsky |
| 2,835,905 A | 5/1958 | Tomasson |
| 2,880,428 A | 4/1959 | Forsland |
| 3,648,308 A | 3/1972 | Greenawalt |
| 3,829,917 A | 8/1974 | De Laittre et al. |
| 3,842,453 A | 10/1974 | Redfield |

(Continued)

FOREIGN PATENT DOCUMENTS

| | | |
|---|---|---|
| CN | 88203329 U | 12/1988 |
| CN | 2071030 U | 2/1991 |

(Continued)

OTHER PUBLICATIONS

International Search Report and Written Opinion of the International Searching Authority dated Dec. 19, 2019 for International Application No. PCT/AU2019/051087.

(Continued)

*Primary Examiner* — David R Hare
*Assistant Examiner* — Madison Emanski
(74) *Attorney, Agent, or Firm* — Mackey Law Firm PLLC

(57) ABSTRACT

A pillow can include a head support surface configured to support at least a portion of a person's head, a first support having a first support surface with a first apex disposed at a first height a second support having a second support surface with a second apex disposed at a second height, and a third support having a third support surface with a third apex disposed at a third height. The support surfaces can support at least a portion of a person's neck when at least a portion of their head is in contact with the head support surface. One or more of the heights can differ from one or more other heights. A pillow can include one or more openings and one or more inserts configured to be disposed therein.

20 Claims, 5 Drawing Sheets

(56) References Cited

U.S. PATENT DOCUMENTS

| | | |
|---|---|---|
| D240,311 S | 6/1976 | Owens |
| D241,104 S | 8/1976 | Copeland |
| D245,298 S | 8/1977 | Brahm |
| D247,406 S | 3/1978 | Stahl et al. |
| D254,029 S | 1/1980 | Barbagallo |
| D255,959 S | 7/1980 | Mitchell |
| D256,408 S | 8/1980 | Nakisbendi |
| 4,218,792 A | 8/1980 | Kogan |
| 4,424,599 A | 1/1984 | Hannouche |
| D276,938 S | 12/1984 | Pedersen |
| 4,494,261 A | 1/1985 | Morrow |
| 4,513,462 A | 4/1985 | Thomas |
| 4,550,459 A | 11/1985 | Endel et al. |
| D286,586 S | 11/1986 | Radford |
| 4,679,263 A | 7/1987 | Honer |
| 4,754,513 A | 7/1988 | Rinz |
| 4,756,090 A | 7/1988 | Pedrow |
| 4,759,089 A | 7/1988 | Fox |
| 4,777,678 A | 10/1988 | Moore |
| 4,805,603 A | 2/1989 | Cumberland |
| 4,821,355 A | 4/1989 | Burkhardt |
| 4,829,614 A | 5/1989 | Harper |
| 4,832,007 A | 5/1989 | Davis, Jr. et al. |
| 4,916,765 A | 4/1990 | Castronovo, Jr. |
| D308,141 S | 5/1990 | Genova et al. |
| 4,928,335 A | 5/1990 | Pedrow |
| D310,609 S | 9/1990 | Burkhardt |
| 4,956,886 A | 9/1990 | Sarkozi |
| D314,284 S | 2/1991 | Cohen |
| D317,840 S | 7/1991 | Jagdat |
| 5,123,132 A | 6/1992 | Dixon |
| 5,127,120 A | 7/1992 | Mason |
| D334,107 S | 3/1993 | Johnson |
| D337,210 S | 7/1993 | Silverman |
| 5,237,714 A | 8/1993 | Baron |
| D341,267 S | 11/1993 | Caldwell |
| 5,279,310 A | 1/1994 | Hsien |
| 5,363,524 A | 11/1994 | Lang |
| D361,905 S | 9/1995 | Adams et al. |
| 5,457,832 A | 10/1995 | Tatum |
| 5,481,771 A | 1/1996 | Burk, IV |
| D366,966 S | 2/1996 | Bonaddio et al. |
| D370,821 S | 6/1996 | Mata |
| D372,805 S | 8/1996 | Bonaddio et al. |
| D375,417 S | 11/1996 | Bonaddio et al. |
| 5,630,651 A | 5/1997 | Fishbane |
| 5,664,810 A | 7/1997 | Kato |
| 5,662,597 A | 9/1997 | Chitwood |
| 5,694,726 A | 12/1997 | Wu |
| 5,708,998 A | 1/1998 | Torbik |
| 5,727,267 A | 3/1998 | Keilhauer |
| 5,797,154 A | 8/1998 | Contreras |
| 5,809,594 A | 9/1998 | Isogai |
| 5,819,485 A | 10/1998 | Lane et al. |
| D400,386 S | 11/1998 | Keilhauer |
| D400,387 S | 11/1998 | Denney |
| D404,238 S | 1/1999 | Keilhauer |
| D405,854 S | 2/1999 | Grant |
| D410,744 S | 6/1999 | Banister |
| 5,916,185 A | 6/1999 | Chitwood |
| 6,000,401 A | 12/1999 | Herrick |
| D418,897 S | 1/2000 | Rembles |
| D444,560 S | 7/2001 | Berglund |
| D447,253 S | 8/2001 | Gardner |
| D447,577 S | 9/2001 | Gardner |
| D448,581 S | 10/2001 | Branch |
| D448,582 S | 10/2001 | Branch |
| 6,345,401 B1 | 2/2002 | Frydman |
| D454,180 S | 3/2002 | Wessels |
| 6,381,784 B1 | 5/2002 | Davis et al. |
| D458,049 S | 6/2002 | Prins et al. |
| D461,649 S | 8/2002 | Prins et al. |
| 6,446,288 B1 | 9/2002 | Pi |
| 6,471,726 B2 | 10/2002 | Wang |
| D473,063 S | 4/2003 | Pappas |
| D480,484 S | 10/2003 | Kakhiani |
| D484,618 S | 12/2003 | Kakhiani |
| D486,247 S | 2/2004 | Eichner et al. |
| 6,704,957 B2 | 3/2004 | Rhodes |
| D491,282 S | 6/2004 | Kakhiani |
| 6,751,818 B2 | 6/2004 | Troop |
| 6,817,049 B1 | 11/2004 | Hall |
| D499,816 S | 12/2004 | Eichner et al. |
| D510,631 S | 10/2005 | Hsu |
| 6,981,288 B1 * | 1/2006 | Hu ............................ A47G 9/10 5/636 |
| 7,013,512 B1 | 3/2006 | Hsu |
| D518,576 S | 4/2006 | Sevier et al. |
| D521,301 S | 5/2006 | Dickson |
| 7,082,633 B1 | 8/2006 | Maarbjerg |
| D531,315 S | 10/2006 | Caudra |
| D551,355 S | 9/2007 | Tao |
| D555,408 S | 11/2007 | Keilhauer |
| D573,830 S | 7/2008 | Kalatsky |
| D595,527 S | 7/2009 | Carter |
| D597,743 S | 8/2009 | Skinner |
| 7,578,015 B1 * | 8/2009 | Wilson ................. A47G 9/1036 5/636 |
| D615,210 S | 5/2010 | Woodhams et al. |
| D618,354 S | 6/2010 | Francucci et al. |
| D619,404 S | 7/2010 | Castillo |
| D623,305 S | 9/2010 | Tao |
| D635,265 S | 3/2011 | Coffey et al. |
| D635,271 S | 3/2011 | Azar et al. |
| D637,030 S | 5/2011 | Khandai |
| D638,646 S | 5/2011 | Penza |
| D646,498 S | 10/2011 | Blasini et al. |
| D651,368 S | 12/2011 | Seliskar et al. |
| 8,161,588 B1 * | 4/2012 | Anson ..................... A47G 9/109 5/636 |
| D664,256 S | 7/2012 | Dennewald |
| D665,503 S | 8/2012 | Dennewald |
| D672,879 S | 12/2012 | Hawkins |
| D678,539 S | 3/2013 | Narson |
| 8,393,027 B2 | 3/2013 | Weisberg |
| D680,654 S | 4/2013 | Borreli |
| D681,994 S | 5/2013 | Morgan, II |
| D684,394 S | 6/2013 | Leemkuil |
| D688,379 S | 8/2013 | Ehlers |
| D701,710 S | 4/2014 | Martinez |
| 8,713,732 B2 | 5/2014 | Dennewald |
| D708,754 S | 7/2014 | Harangvolgyi |
| D710,021 S | 7/2014 | Blaine et al. |
| D715,452 S | 10/2014 | Schiavon |
| D736,397 S | 8/2015 | McAviney et al. |
| D739,036 S | 9/2015 | McAviney et al. |
| 9,186,004 B2 | 11/2015 | Dennewald |
| D745,786 S | 12/2015 | Ko |
| D748,406 S | 2/2016 | Pham |
| D751,314 S | 3/2016 | Meyer |
| D764,062 S | 8/2016 | Dennewald |
| 10,561,561 B2 * | 2/2020 | Kim ....................... A61H 1/008 |
| 2004/0006822 A1 | 1/2004 | Milligan |
| 2004/0068799 A1 | 4/2004 | Wilson |
| 2004/0194214 A1 | 10/2004 | Troop |
| 2005/0060807 A1 | 3/2005 | Kaizuka |
| 2005/0177944 A1 | 8/2005 | Kang et al. |
| 2007/0101503 A1 | 5/2007 | Dennewald |
| 2007/0113348 A1 | 5/2007 | Ramaiah |
| 2008/0115284 A1 | 5/2008 | Hiatt |
| 2008/0134438 A1 * | 6/2008 | Park ......................... A47G 9/10 5/636 |
| 2011/0162146 A1 | 7/2011 | Frydman |
| 2014/0076330 A1 | 3/2014 | Rolle et al. |

FOREIGN PATENT DOCUMENTS

| | | |
|---|---|---|
| CN | 2505048 Y | 8/2002 |
| CN | 2812877 Y | 9/2006 |
| CN | 2824881 Y | 10/2006 |
| CN | 2850576 Y | 12/2006 |

(56) References Cited

FOREIGN PATENT DOCUMENTS

| | | |
|---|---|---|
| JP | 3102917 U | 4/2004 |
| JP | 3108760 U | 2/2005 |

OTHER PUBLICATIONS

Printouts from https://completesleeprrr.com/; last accessed Jul. 8, 2020.

* cited by examiner

CAVITY CONTOUR PILLOW

CROSS REFERENCE TO RELATED APPLICATIONS

This application claims the benefit of U.S. Provisional Patent Application No. 62/735,195 filed Sep. 24, 2018, the entire contents of which are hereby incorporated by reference herein.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The inventions disclosed and taught herein relate generally to pillows; and more specifically relate to contour pillows.

General Background

Chiropractors have for many years studied the biomechanics of the spine and the adverse effects of reduced motion in the joints of the spine. A person's physical movement can become restricted when soft tissue structures alter, commonly due to contraction of the soft tissue structures. These soft tissue structures comprise, among other things, ligaments, joint capsules, muscles and tendons.

Prolonged poor posture or trauma can create stresses that effect normal motion of the spine. These stresses can encourage structural changes, altering the spine's optimal functional position. This can result is inefficient biomechanics and a decrease in the movement in the joints of the spine.

When structural changes occur in the spine, the surrounding soft tissue structures can also change due to their altered position. This altered position of the spine and surrounding soft tissue structures exacerbates poor movement, encouraging the spinal joints further away from optimal functioning. In the cervical spine, this process is evident when the normal lordotic position is decreased. This can be visualized via diagnostic imaging using an X-ray analysis.

One thing that can contribute to or even aggravate musculoskeletal issues with the shoulders, neck and cervical spine is a person's pillow. Humans spend significant portions of their lives asleep and commonly rest their heads on pillows when resting or sleeping. Conventional pillows, such as those filled with down feathers or cotton, can be comfortable but often do not support or facilitate normal lordosis of the cervical spine. Moreover, while various devices exist for treating abnormal lordosis, such as the cervical Denneroll® orthotic device available from Denneroll Industries International Pty Limited (Wheeler Heights, Australia), such devices are not necessarily intended for use during sleep and at least some people may not consider such devices comfortable enough to sleep on in the first instance. In addition, while a number of contour pillows are commercially available, such contour pillows tend to have limited or no adjustability and/or flexibility (e.g., in terms of positions of use) and tend to have limited abilities to accommodate users of different sizes or neck presentations or to provide a given user with a number of options for positioning, comfort level and/or function.

The embodiments disclosed and taught herein are directed to improved pillow devices, systems and methods for providing users with an improved balance between functionality and comfort, which can include providing a user with multiple options with regard to pillow configuration, positioning and/or functionality. In at least one embodiment, a pillow according to the disclosure can support a normal, healthy lordosis of the cervical spine during sleep and can do so with variable intensity by way of interchangeable inserts. In at least one embodiment, a pillow according to the disclosure can provide users with a number of options for positioning, comfort level and/or function.

Any reference in this specification to any known or existing device, information or thing is not, and should not be taken as, an acknowledgment, admission or suggestion that such device, information or thing forms part of the prior art or common general knowledge in the field of endeavor to which this application relates. Rather, the foregoing information is introductory in nature and is intended to help provide the reader with background information that may facilitate a better understanding of one or more aspects of the embodiments of the present disclosure.

BRIEF SUMMARY OF THE INVENTION

In at least one embodiment, a pillow can include a base, a front terminal end, a rear terminal end, two or more sides, a head support surface adapted to support at least a portion of a person's head, wherein at least a portion of the head support surface can be disposed at a head support height above the base, a first support having a first support surface with a first apex disposed at a first height above the base, a second support having a second support surface with a second apex disposed at a second height above the base, and a third support having a third support surface with a third apex disposed at a third height above the base.

In at least one embodiment, a first support surface can be disposed on a side between the front and rear terminal ends and can be adapted to support at least a portion of a person's neck when the person can be lying supine with at least a portion of their neck in contact with the first support and at least a portion of their head in contact with the head support surface. A second support surface can be disposed on another side between the front and rear terminal ends and can be adapted to support at least a portion of a person's neck when the person is lying supine with at least a portion of their neck in contact with the second support and at least a portion of their head in contact with the head support surface. A third support surface can be disposed frontward of the rear terminal end between two or more sides (e.g., first, second, left, right, or other sides) and can be adapted to support at least a portion of a person's neck when the person is lying supine with at least a portion of their neck in contact with the third support and at least a portion of their head in contact with the head support surface. One or more heights, such as one or more of a first, second or third height can be greater than a head support height.

In at least one embodiment, one or more heights, which can include at least two of the first, second and third heights can be different. In at least one embodiment, each of the first, second and third heights are different. In at least one embodiment, a pillow can include a recess disposed between or otherwise relative to one or more surfaces or other components or portions of a pillow, such as a third or other support and a head support surface or portion thereof. In at least one embodiment, a pillow can include one or more openings, such as a partial or through opening, disposed between or otherwise relative to one or more surfaces or supports, such as at least partially between a third support and a head support surface. In at least one embodiment, a pillow can include one or more surfaces, such as a head support surface, which can include one or more grooves or other recesses or openings, such as a plurality of grooves, which can include one or more parallel or transverse grooves. In at least one embodiment, a plurality of grooves can be disposed between the front terminal end and the third support, separately or in combination, in whole or in part. In at least one embodiment, at least one of a plurality of grooves can be transverse to the front terminal end.

In at least one embodiment, a pillow can include one or more cavities in the base, such as one or more cavities that extend into at least one of the first, second and third supports, or into another portion of the pillow. One or more cavities can be adapted to receive at least a portion of an insert. A pillow can include one or more inserts, such as of the same or different sizes, shapes, materials, etc., which can include one or more inserts adapted to couple with one or more cavities.

In at least one embodiment, a pillow can include supports or support surfaces of one or more heights. In at least one embodiment, a first height can be less than a second height and a second height can be less than a third height. At least a portion of a third or other support surface can be disposed between or otherwise relative to a rear end or rear terminal end and at least one of first and second or other support surfaces.

A third support surface can intersect or otherwise cooperate with at least one of a first, second, or other support surface. At least a portion of one or more of the first, second and third support surfaces, or another surface, can be convex, concave, contoured, or otherwise shaped for supporting a person's body or portion thereof. In at least one embodiment, a pillow can include a transition or other surface(s) disposed at least partially between a head support surface and a front end or front terminal end.

In at least one embodiment, a pillow can include at least one of a recess and a through opening disposed between, in or otherwise relative to one or more supports or surfaces, such as a third support and a head support surface. A recess or opening can be adapted for receiving at least a portion of a person's head, which can include at least a portion of the crown of a person's head, such as, for example, when the person is lying supine or in another position, which can include lying on their side, such as with at least a portion of their neck in contact with one or more supports or support surfaces, such as the third or another support, and such as with at least a portion of their head in contact with, for example, the head support surface or a portion thereof, which in at least one embodiment can include at least a portion of a recess or opening.

In at least one embodiment, a pillow can include at least one of a recess and a through opening disposed between, in or otherwise relative to one or more supports or surfaces, such as a third support and a head support surface. A recess or opening can be adapted for receiving at least a portion of a person's head, which can include at least a portion of the crown of a person's head, such as, for example, when the person is lying supine or in another position, which can include lying on their side, such as with at least a portion of their neck in contact with one or more supports or support surfaces, such as any of the first and second supports, and, for example, at least a portion of their head in contact with a front side of the third support and at least a portion of their head in contact with at least a portion of the head support surface that is nearest, part of, or otherwise disposed relative to a recess or opening.

In at least one embodiment, a pillow can include one or more supports comprising one or more walls or other portions, such as inwardly or otherwise facing walls. One or more walls can be adapted for contacting one or more portions of a person, such as, for example, opposite sides of a person's head, such as when the person is lying supine or otherwise with at least a portion of their neck in contact with one or more supports, such as a third support, and at least a portion of their head in contact with a head support surface.

In at least one embodiment, a pillow according to the disclosure can include a base, a front terminal end, a rear terminal end, a first side, a second side, a neck support and an opening for allowing at least a portion of a person's head to be disposed in or through the opening when the person is lying supine with at least a portion of the person's neck in contact with at least a portion of the neck support. In at least one embodiment, a pillow can have an opening configured for allowing at least a portion of a person's head to pass through the opening and pillow and into contact with a substrate surface beneath the pillow and/or person, such as a bed, table or floor. A pillow can but need not include one or more other neck supports disposed about the opening. A pillow can include a head support surface disposed next to the opening and/or the opening can be disposed in or through a head support portion of the pillow. One or more sides of a pillow can include a raised neck support in communication with an opening in or through the pillow. In at least one embodiment, a pillow according to the disclosure can include one neck support. In at least one embodiment, a pillow according to the disclosure can include more than one neck support. In at least one embodiment, a pillow according to the disclosure can be configured to support at least a portion of a person's neck and/or head while at least a portion of the person's head is supported by or on substrate surface under the pillow. In at least one embodiment, a pillow according to the disclosure can include a head support having a base, at least one opening in or through the head support, and at least one neck support disposed for supporting a person's neck when the person is lying on the pillow supine with a portion of their head disposed in or through the opening.

DETAILED DESCRIPTION OF THE INVENTION

Figure 1:
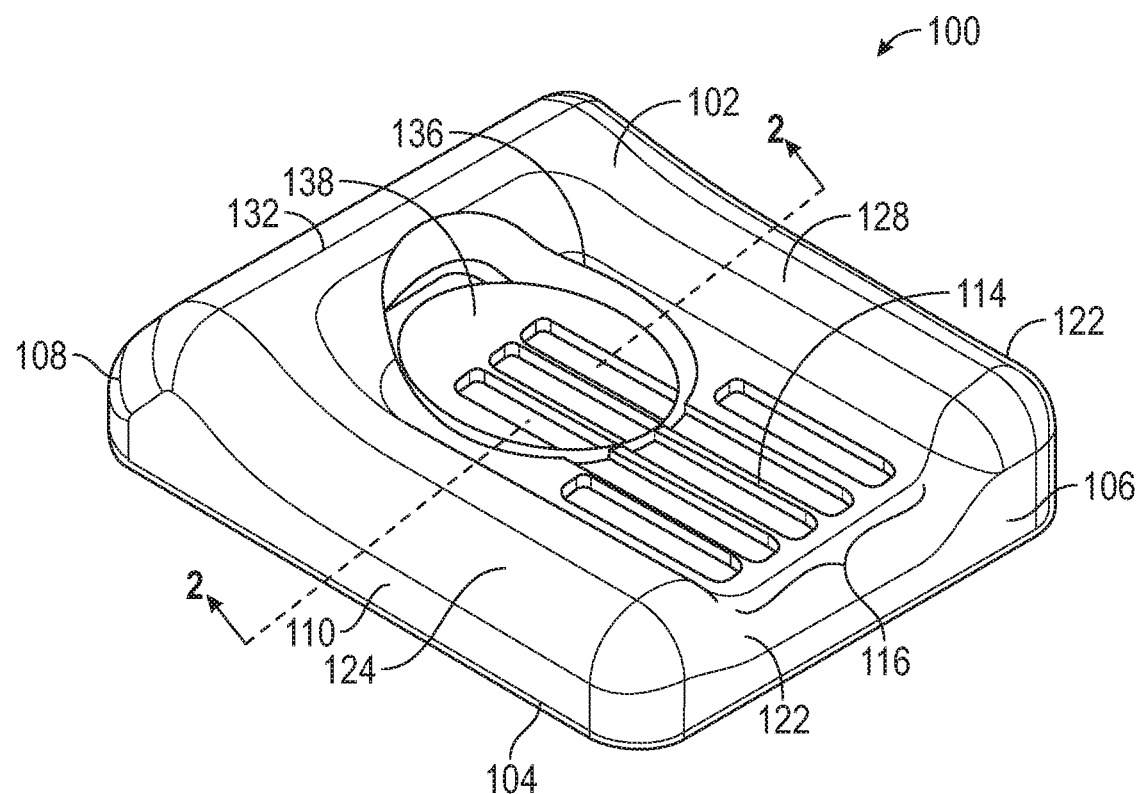
FIG. 1 is a top perspective view of one of many embodiments of a pillow according to the disclosure.

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the disclosure are described or shown for the sake of clarity and understanding. Persons of skill in this art will also appreciate that the development of an actual commercial embodiment incorporating aspects of the present disclosure will require numerous implementation-specific decisions to achieve the developer's ultimate goals for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having the benefits of this disclosure. The inventions disclosed and taught herein are susceptible to numerous and various modifications and alternative forms. The use of a singular term, such as, but not limited to, "a," is not intended as limiting of the number of items. Also, the use of relational terms, such as, but not limited to, "top," "bottom," "left," "right," "upper," "lower," "down," "up," "side," "first," "second" and the like are used in the written description for clarity and/or in specific reference to the Figures and are not intended to limit the scope of the inventions or the appended claims. The terms "including" and "such as" are illustrative and not limitative.

The terms "couple," "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and can further include without limitation integrally forming one functional member with another in a unity fashion. The coupling can occur in any direction, including rotationally. The term "can" as used herein means "can but need not" unless otherwise indicated. The terms "and" and "or" as used herein mean "and/or" unless otherwise indicated.

Applicant has created new and useful devices, systems and methods for supporting a person's head and/or neck. One or more embodiments of the disclosure can provide users with an improved balance between functionality and comfort, which can include providing a user with multiple options with regard to configuration, positioning and/or functionality. One or more embodiments of the disclosure can include a plurality of support surfaces for supporting a person's head and/or neck in a plurality of ways. One or more embodiments of the disclosure can be adapted for supporting a person's head and/or neck in a plurality of manners, two or more of which can differ and can vary depending upon which side of a pillow a person chooses to use or how a person chooses to position a pillow relative to his or her body or vice versa. One or more embodiments of the disclosure can provide users with optional configurations, which can include configurations that vary in function, such as between stretching and support or intensities thereof.

Figure 2:
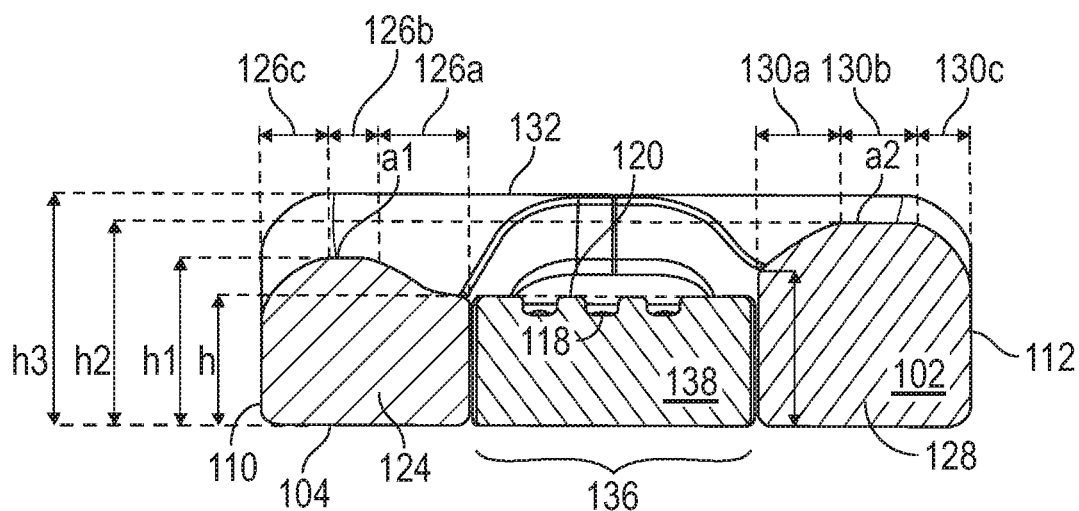
FIG. 2 is a cross-sectional view of the embodiment of FIG. 1.
Figure 3:
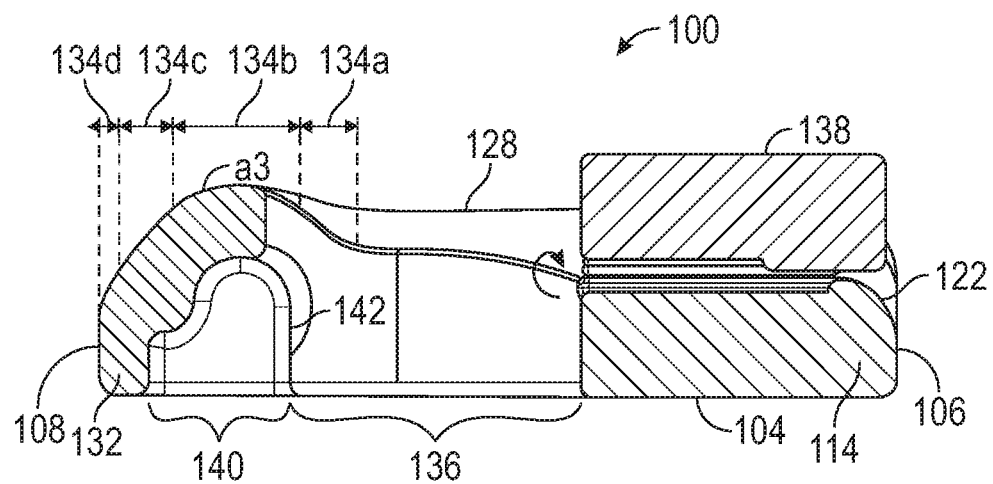
FIG. 3 is another cross-sectional view of the embodiment of FIG. 1.
Figure 4:
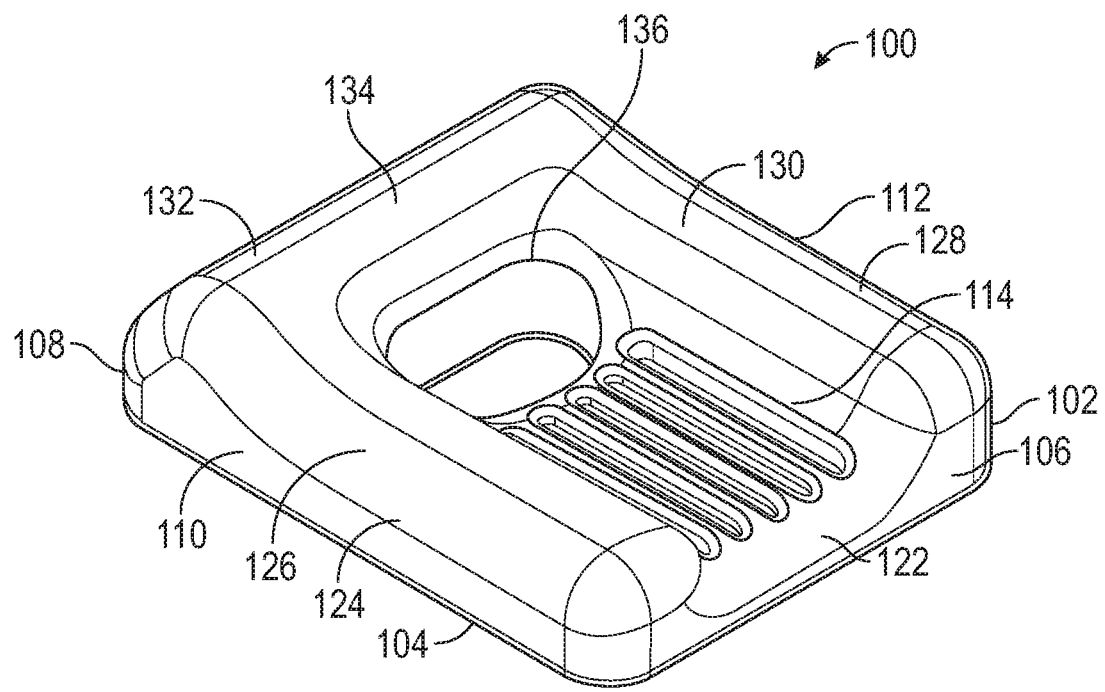
FIG. 4 is a top perspective view of another of many embodiments of a pillow according to the disclosure.
Figure 5:
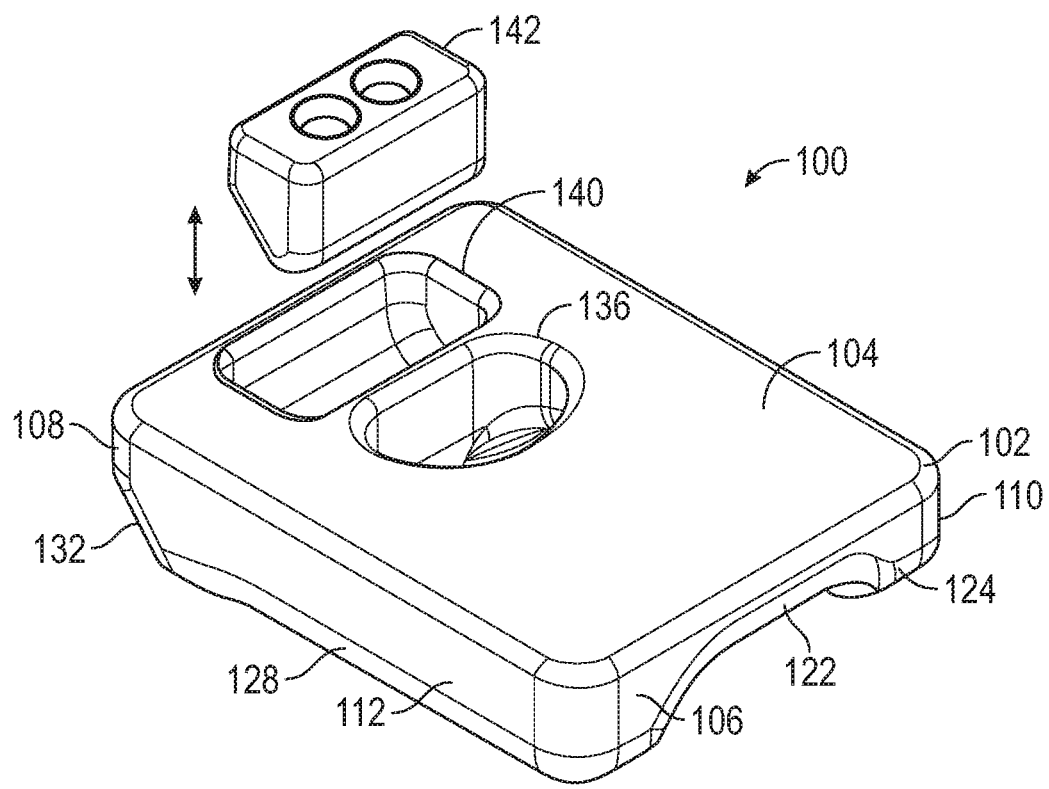
FIG. 5 is a bottom perspective view of the embodiment of FIG. 4.
Figure 6:
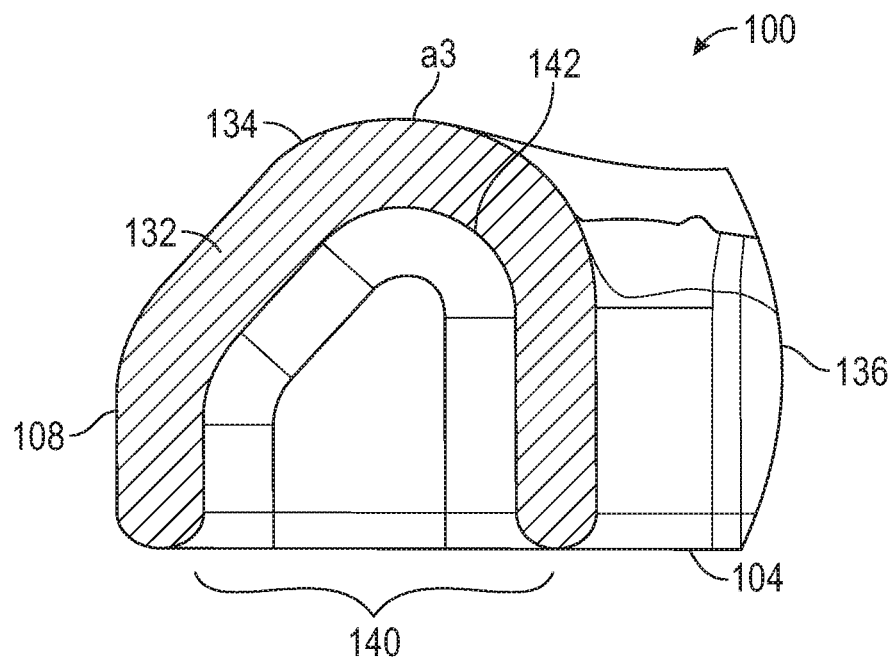
FIG. 6 is a partial cross-sectional view of the embodiment of FIG. 5.
Figure 7:
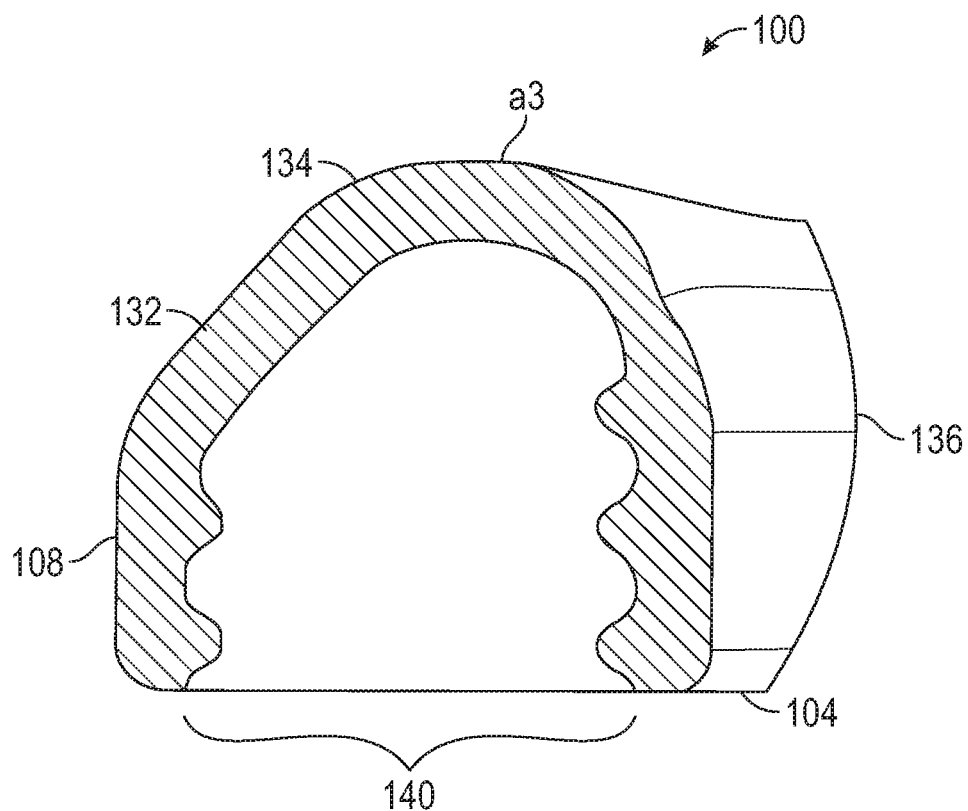
FIG. 7 is a partial cross-sectional view of another of many embodiments of a pillow according to the disclosure.
Figure 8:
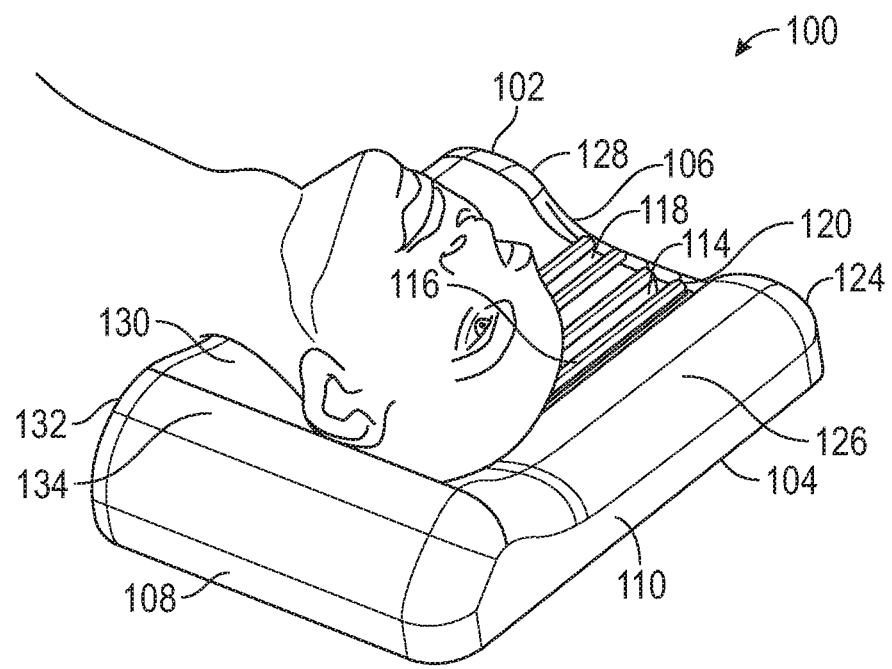
FIG. 8 is a top perspective view of an individual utilizing one of many embodiments of a pillow according to the disclosure in one of many positions.
Figure 9:
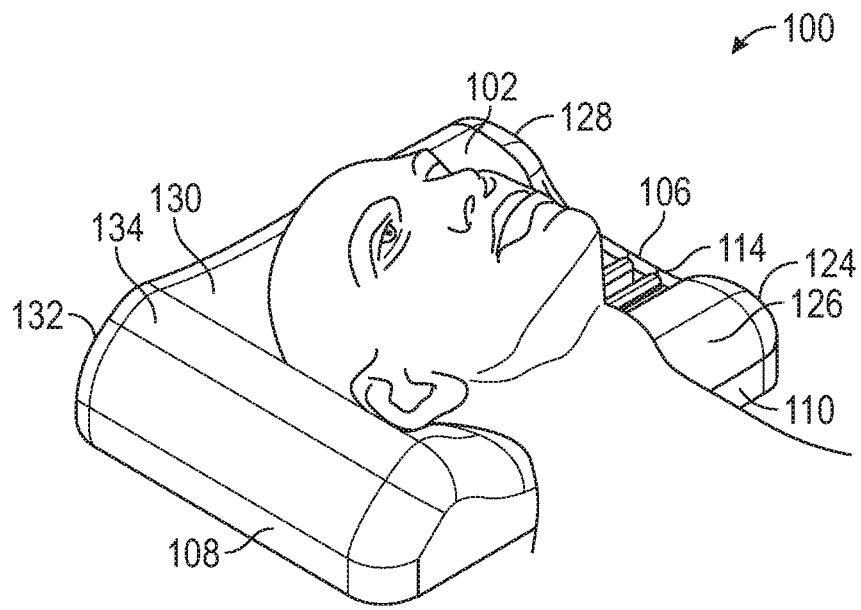
FIG. 9 is a top perspective view of an individual utilizing one of many embodiments of a pillow according to the disclosure in another of many positions.
Figure 10:
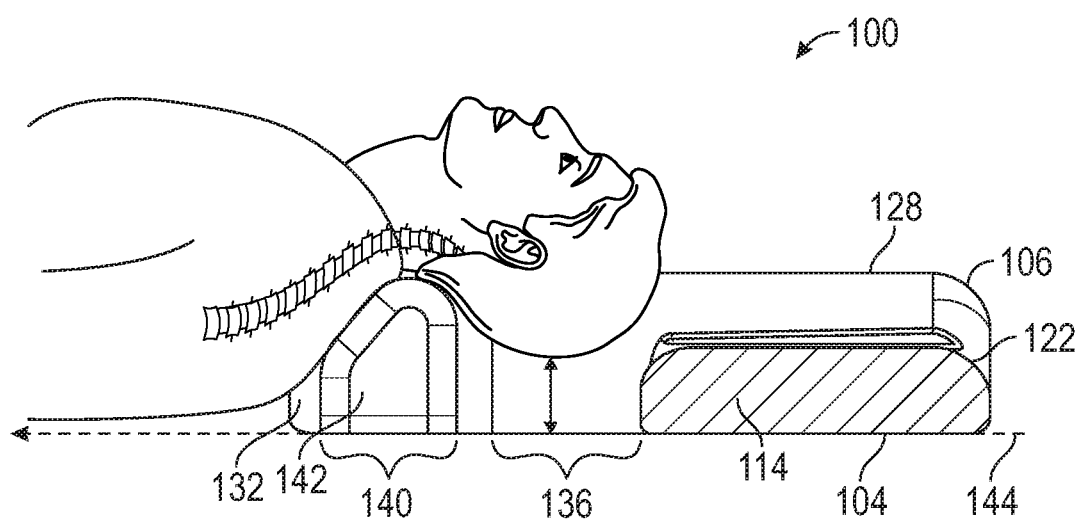
FIG. 10 is a top perspective view of an individual utilizing one of many embodiments of a pillow according to the disclosure in yet another of many positions.

FIG. 1 is a top perspective view of one of many embodiments of a pillow according to the disclosure. FIG. 2 is a cross-sectional view of the embodiment of FIG. 1. FIG. 3 is another cross-sectional view of the embodiment of FIG. 1. FIG. 4 is a top perspective view of another of many embodiments of a pillow according to the disclosure. FIG. 5 is a bottom perspective view of the embodiment of FIG. 4. FIG. 6 is a partial cross-sectional view of the embodiment of FIG. 5. FIG. 7 is a partial cross-sectional view of another of many embodiments of a pillow according to the disclosure. FIG. 8 is a top perspective view of an individual utilizing one of many embodiments of a pillow according to the disclosure in one of many positions. FIG. 9 is a top perspective view of an individual utilizing one of many embodiments of a pillow according to the disclosure in another of many positions. FIG. 10 is a top perspective view of an individual utilizing one of many embodiments of a pillow according to the disclosure in yet another of many positions. FIGS. 1-10 will be described in conjunction with one another.

In at least one embodiment, a device or system 100 according to the disclosure, which can be or include a pillow, pillow device or pillow system (hereinafter referred to as "pillow 100"), can be adapted for supporting or otherwise holding at least a portion of a person's neck and/or head in one or more positions. In at least one embodiment, pillow 100 can be or include a unitary body 102; however, this need not be the case and, in at least one embodiment, pillow 100 can be or include a body 102 comprised of two or more bodies or body portions coupled to one another. Pillow 100 can include one or more bases 104 for supporting one or more portions or components of pillow 100 on a surface or structure on which pillow 100 sits, such as a floor, table, bed, or other substrate on which a person may wish to utilize pillow 100. Base 104 can, but need not, be at least partially flat or planar, and can but need not be wholly continuous (which can include surfaces in one plane or more than one plane). In at least one embodiment, base 104 can have one or more openings therein or there through, as described in further detail below.

Pillow 100 can include one or more sides (or ends), which can include terminal sides, ends or portions thereof. Pillow 100 can include any number of sides according to an implementation of the disclosure, which can be or include any number of terminations or other boundaries according to an implementation of the disclosure, whether exterior, interior, top, bottom, front, rear, lateral, or otherwise. In at least one embodiment, pillow 100 can be square or rectangular (i.e., at least generally or substantially square or rectangular) and can have or include four sides, such as a front end 106, a rear end 108, a first side 110 and a second side 112 (e.g., left and right sides, or vice versa). As illustrated in the figures for illustrative purposes, in at least one embodiment, which is but one of many, one or more of sides 106, 108, 110, 112 can be at least partially flat or planar or, as another example, at least partially curved or otherwise contoured, which can but need not include having a radiused or otherwise nonlinear transition with one or more other portions of pillow 100 (e.g., base 104, one or more top surfaces of pillow 100, or one another). Similarly, one or more of sides 106, 108, 110, 112 can be at least partially vertical or perpendicular to (i.e., at least generally or substantially vertical or perpendicular to) base 104, such as when pillow 100 is disposed right side up on a horizontal surface. However, this need not be the case and, in at least one embodiment, one or more of sides 106, 108, 110, 112 can be at least partially disposed at an angle relative to horizontal (or another reference, such as vertical).

Pillow 100 can include one or more supports having support surfaces for supporting one or more portions of a person's body during use, such as all or a portion of a person's neck and/or head. While one or more supports or support surfaces can be continuous or contiguous in whole or in part, they may nonetheless be referenced or described as respective supports or support surfaces for purposes of clarity and convenience of reference. In other words, for instance, in at least one embodiment, body 102 or a portion thereof can be unitary and a top or other surface can be continuous while nonetheless varying in some manner (e.g., height, shape, contour, etc.) from one area or portion to another; while such a surface can be referred to as a single surface in at least one sense, it can also be referred to as a plurality of surfaces or surface portions that collectively form or constitute all or a portion of pillow 100, as the case may be.

In at least one embodiment, pillow 100 can include one or more head supports 114 having one or more surfaces, such as a head support surface 116, for supporting at least a portion of a person's head during utilization of pillow 100 in accordance with the present disclosure. Head support 114 and head support surface 116 can be sized and shaped for allowing all or a portion of a person's head to be disposed thereon, which can include being at least generally rectangular as illustrated in the figures for exemplary purposes but need not and can alternatively or collectively include being at least generally circular, oblong, irregular, or another shape. Head support surface 116 can be at least partially flat but need not be and alternatively or collectively can be at least partially curved or contoured, which can include, for example, being at least partially concave or convex. In at least one embodiment, which is but one of many, head support surface 116 can include one or more grooves 118, such as openings or slots, and/or one or more ridges 120, such as extensions or walls, for reducing or minimizing the surface area or contact area in contact with a person's head during use. In at least one embodiment, head support surface 116 can extend to front end 106, which can but need not include a curved, ramped or otherwise shaped transition 122 from head support surface 116 to front end 106 or vice versa. One or more grooves 118 and/or ridges 120 (if present) can extend all the way to front end 106 or, as another example, can terminate short of front end 106 or another portion of pillow 100, such as transition 122. In at least one embodiment, transition 122 can be sized and shaped for supporting at least a portion of a person's neck and/or upper back/shoulders during use, whether separately or in combination with one or more of head support surface 116 and front end 106. All or a portion of head support surface 116 can be disposed one or more distances from base 104 or a portion thereof. For example, pillow 100 can include one or more heights, such as a head support height h, and at least a portion of head support surface 116 can be disposed at height h (which can but need not be or include an apex height of head support 114), which can be any dimension according to an implementation of the disclosure.

In at least one embodiment, pillow 100 can include one or more neck supports having one or more surfaces for supporting at least a portion of a person's neck during utilization of pillow 100 in accordance with the present disclosure. For example, in at least one preferred embodiment, which is but one of many, pillow 100 can have a first neck support 124 having a first neck support surface 126, a second neck support 128 having a second neck support surface 130, and a third neck support 132 having a third neck support surface 134. First, second and third supports 124, 128, 132 and/or first, second and third support surfaces 126, 130, 134 can have respective apexes a1, a2, a3 disposed at respective heights h1, h2, h3, which can be or include any dimensions according to an implementation of the disclosure. In at least one embodiment, each of heights h1, h2, h3 can be greater than height h of head support 114. In at least one embodiment, two or more of heights h1, h2, h3 can be the same. In at least one embodiment, two or more of heights h1, h2, h3 can be different. In at least one embodiment, all of heights h1, h2, h3 can be different. As shown in the embodiment of, e.g., FIG. 2 for illustrative purposes, which embodiment is but one of many, in at least one embodiment, height h1 can be less than height h2 and height h2 can be less than height h3. However, this need not be the case and, in at least one embodiment, the relative heights of heights h1, h2, h3 can be otherwise arranged or configured. For instance, any one or more of first, second and third supports 124, 128, 132 can be the tallest, any one or more of first, second and third supports 124, 128, 132 can be the shortest, and any one or more of first, second and third supports 124, 128, 132 can be taller or shorter than any other one of first, second and third supports 124, 128, 132, as desired according to an implementation of the disclosure.

Furthermore, as illustrated in the exemplary embodiments of the Figures, which are but some of many, in at least one embodiment, one or more of first, second and third support surfaces 126, 130, 134 can have a uniform height along all or a portion of its length. However, this need not be the case and, in at least one embodiment, one or more of first, second and third support surfaces 126, 130, 134 can have a height that changes along all or a portion of its length. As another example, one or more of first, second and third support surfaces 126, 130, 134 can include two or more component surfaces, subsurfaces or surface portions that can differ in height (or otherwise, such as shape) relative to one another. Thus, for instance, in at least one embodiment, rather than having three support surface apex heights as in the exemplary embodiments of the Figures, one or more of neck supports 124, 128, 132 can include a plurality of support surfaces having a plurality of respective apex heights and pillow 100 can thereby include one or more neck support surfaces having a different apex height (not shown) than that of all of a portion of one or more of first, second and third support surfaces 126, 130, 134.

One or more neck supports, such as first, second and third neck supports 124, 128, 132, can be disposed about or otherwise relative to head support 114 for supporting a person's neck when the person is lying down (e.g., supine on their back or on their side) with their head situated on or otherwise supported by pillow 100 or a portion thereof and the remainder of their body situated outwardly from pillow 100 (e.g., radially outwardly about an axis perpendicular to base 104; see, e.g., FIGS. 8-10). In at least one embodiment, one or more of first, second and third neck supports 124, 128, 132 can at least generally bound at least a portion of head support 114. For example, one of first, second and third neck supports 124, 128, 132 can be disposed on or constitute one side of pillow 100, another of neck supports 124, 128, 132 can be disposed on or constitute another side of pillow 100, and yet another of neck supports 124, 128, 132 can be disposed on or constitute yet another side of pillow 100. As illustrated in the exemplary embodiments shown in the Figures, in at least one embodiment, first, second and third neck supports 124, 128, 132 can be situated on the left, right and rear sides of pillow 100, respectively. However, this need not be the case and, in at least one embodiment, any of first, second and third neck supports 124, 128, 132 can be disposed on any side of pillow 100 desired for an implementation of the disclosure. One or more of first, second and third neck supports 124, 128, 132 can but need not intersect or otherwise contact one another, which can but need not include being formed integrally with one another. In at least one embodiment, pillow 100 can have four sides and two or more of first, second and third neck supports 124, 128, 132 can be perpendicular (i.e., at least generally or substantially perpendicular) to one another. However, this need not be the case and any two or more of first, second and third neck supports 124, 128, 132 can be disposed at another angle relative to one another if desired for an implementation of the disclosure, which can be or include any angle (e.g., from 0 to 90 degrees). As another example, in at least one embodiment, pillow 100 can have more or less than four sides, such as three sides, five sides, or more sides. For instance, in at least one embodiment, pillow 100 can be at least generally triangular and one or more of sides 110, 112, ends 106, 108, transition 122 and/or first, second and third neck supports 124, 128, 132 can be absent.

One or more of first, second and third support surfaces 126, 130, 134 (including any additional or component support surfaces, if present) can be shaped and arranged for supporting at least a portion of a person's neck during use of pillow 100 in one or more positions. In at least one embodiment, one or more of first, second and third support surfaces 126, 130, 134 (including any additional or component support surfaces, if present) can advantageously be shaped and arranged for supporting at least a portion of a person's neck in a manner that strikes a unique balance between comfort and the promotion of healthy or normal lordosis. In at least one embodiment, two or more of first, second and third support surfaces 126, 130, 134 can have shapes, such as cross-sectional shapes, that are the same or similar to one another. In at least one embodiment, two or more of first, second and third support surfaces 126, 130, 134 can have shapes, such as cross-sectional shapes, that differ from one another.

In at least one embodiment, one or more support surfaces can be contoured and can include a profile comprising two or more portions or sections, which can be contiguous with one another and which can collectively make up a continuous (or discontinuous) support surface. Adjacent or continuous portions or sections of a profile can meet, for example, at an intersection or point of transition for two different contour or profile shapes (e.g., two portions having different radiuses, a change from concave to convex, etc.). For example, as best seen in FIG. 2, first neck support surface 126 can include a first portion 126a, a second portion 126b and a third portion 126c. In at least one embodiment, first portion 126a can be at least partially concave, second portion 126b can be at least partially convex, and third portion 126c can be at least partially convex. Apex a1 can be located along second portion 126b at height h1, which can be any height according to an implementation of the disclosure. Any of first, second and third portions 126a, 126b, 126c can have one or more radiuses and/or degrees of curvature, any or all of which can be the same or different. In at least one embodiment, at least a portion of one or more of first, second and third portions 126a, 126b, 126c can be at least partially linear or flat. In at least one embodiment, first neck support surface 126 can include one or more additional surface portions or sections as well, which can be or include subsections of or additions to first, second and third portions 126a, 126b, 126c.

As another example, as best seen in FIG. 2, second neck support surface 130 can include a first portion 130a, a second portion 130b and a third portion 130c. In at least one embodiment, first portion 130a can be at least partially concave, second portion 130b can be at least partially convex, and third portion 130c can be at least partially convex. Apex a2 can be located along second portion 130b at height h2, which can be any height according to an implementation of the disclosure. Any of first, second and third portions 130a, 130b, 130c can have one or more radiuses and/or degrees of curvature, any or all of which can be the same or different. In at least one embodiment, at least a portion of one or more of first, second and third portions 130a, 130b, 130c can be at least partially linear or flat. In at least one embodiment, second neck support surface 130 can include one or more additional surface portions or sections as well, which can be or include subsections of or additions to first, second and third portions 130a, 130b, 130c.

As yet another example, as best seen in FIG. 3, third neck support surface 134 can include a first portion 134a, a second portion 134b, a third portion 134c and a fourth portion 134d. In at least one embodiment, first portion 134a can be at least partially concave, second portion 134b can be at least partially convex, third portion 134c can be at least partially linear, concave or convex, and fourth portion 134d can be at least partially convex. Apex a3 can be located along second portion 134b at height h3, which can be any height according to an implementation of the disclosure. Any of first, second, third and fourth portions 134a, 134b, 134c, 134d can have one or more radiuses and/or degrees of curvature, any or all of which can be the same or different. In at least one embodiment, at least a portion of one or more of first, second, third and fourth portions 134a, 134b, 134c, 134d can be at least partially linear or flat. In at least one embodiment, third neck support surface 134 can include one or more additional surface portions or sections as well, which can be or include subsections of or additions to first, second, third and fourth portions 134a, 134b, 134c, 134d.

In at least one embodiment, pillow 100 can include one or more openings, such as cavities, partial or through holes, voids or other partial or full openings, for enabling or otherwise supporting one of more aspects of use. For example, in at least one embodiment, pillow 100 can include one or more openings 136 in or through head support 114 or a portion thereof, such as head support surface 116, for allowing at least a portion of a person's head (e.g., at least a portion of the crown) to be disposed beneath or lower than head support height h of head support surface 116 during utilization of pillow 100 in one or more positions (see, e.g., FIGS. 8-10). For instance, in at least some cases a user of pillow 100 may wish to utilize pillow 100 for a purpose other than comfort alone, such as for stretching their neck further or more intensely (e.g., than one typically would during sleep, although some may wish to do so during sleep) for further supporting normal lordosis and soft tissue health. In at least one embodiment, opening 136 can be sized and arranged for facilitating stretching of the neck in such a manner, which can include by way of providing enough clearance (e.g., from one or more support surfaces) for at least a portion of a person's head to be suspended above a substrate surface 144 supporting pillow 100 (e.g., under the force of gravity) while at least a portion of the person's neck is supported by a neck support 124, 128, 132 or portion thereof, such as one of neck support surfaces 126, 130, 134.

In at least one embodiment, such as an embodiment wherein opening 136 is or includes a through opening, pillow 100 or one or more portions thereof (e.g., opening 136 and one or more of neck supports 124, 128, 132), can be sized and arranged for allowing at least a portion of a person's head to pass through opening 136. In such an embodiment, which is but one of many, such an arrangement can advantageously provide for at least a portion of a person's head to contact, rest on or otherwise be supported by a substrate surface 144 beneath pillow 100 (e.g., a person's bed) while the person's neck is supported by a neck support 124, 128, 132 or portion thereof, such as one of neck support surfaces 126, 130, 134. Such an embodiment can advantageously provide for a person's head (e.g., the back or crown of the head when lying supine) to be supported at the same (or at least generally or substantially the same) level as the remainder of the person's body (i.e., from the shoulders or back down) while also holding or otherwise supporting the person's neck and cervical spine in a better or more ideal lordosis position. In other words, in at least one embodiment, pillow 100 can provide an improved balance between comfort and health by supporting one's neck with one of neck supports 124, 128, 132 while simultaneously disposing one's head in supporting cooperation with, or allowing one's head to be at least partially supported by, a mattress or other substrate surface beneath pillow 100 or opening 136. While the foregoing advantages have been described in the context of an embodiment of pillow 100 wherein opening 136 is or includes a through hole, that need not be the case and, in at least one embodiment, pillow 100 can afford the same or similar advantages with an opening 136 that is other than a through hole, such as a partial opening 136 having a lowermost support surface disposed at or near the level of base 104 or, as another example, at a height between base 104 and head support height h of head support 114.

By including a plurality of neck supports at different heights (if present), pillow 100 can provide a user with the ability to choose any of a number of different head and/or neck positions according to the user's particular preference or comfort level in one or more body positions (e.g., supine, prone or on one's side) and/or in one or more positions relative to pillow 100. In at least one embodiment, one or more openings 136 can but need not be disposed at least partially in or through one or more neck supports 124, 128, 132 or a portion thereof, such as, for example, through a portion of the head support side of third neck support 132 (or another neck support), which can help increase the degree of curvature or stretching of a person's neck/cervical spine achievable during use of pillow 100. In at least one embodiment, opening 136 can extend into or otherwise be disposed at least partially through one or more neck supports, such as third neck support 132 (see, e.g., FIG. 1), for allowing at least a portion of a person's head to be disposed in or through opening 136 and/or in contact with substrate surface 144 when the person's neck is supported by such neck support. For instance, opening 136 can be sized and arranged for allowing at least a portion of a person's head to be disposed therein or there through without interference from, e.g., head support 114 or head support surface 116. In at least one embodiment, pillow 100 can be adapted for allowing a person's head to contact two or more support surfaces simultaneously during use of the pillow (e.g., an underlying support surface of the pillow or a substrate and one or more lateral or side surfaces, or two or more lateral or side surfaces, such as the inwardly facing sides of one or more neck supports). In at least one embodiment, pillow 100 can be adapted for allowing at least a portion of a person's head to contact one support surface or no support surfaces in one or more positions of use.

In at least one embodiment, pillow 100 can include one or more inserts 138 for at least optionally filling at least a portion of opening 136 when desired by a user of pillow 100, such as when the added flexibility or additional head travel distance afforded by opening 136 is not in use. When coupled to opening 136, the top (which can but need not include one or more grooves 118 or ridges 120) of insert 138 can be or constitute at least a portion of head support 114 or head support surface 116. Insert 138 can be adapted to couple with body 102 or opening 136 in any manner according to an implementation of the disclosure, such as by friction fit or via the use of one or more fasteners (e.g., hook and loop material). As another example, in at least one embodiment, insert 138 can be hingeably coupled to body 102 and adapted to rotate out of opening 136 (e.g., toward front end 106 and/or onto head support 114) when not in use.

In at least one embodiment, pillow 100 can include one or more openings 140 for receiving at least a portion of one or more other inserts 142 into one or more of neck supports 124, 128, 132. As illustrated in the exemplary embodiments of the Figures, which are but some of many, opening 140 can be disposed in or through base 104 and at least partially into, e.g., third neck support 132, for receiving at least a portion of insert 142 therein. However, this need not be the case, and alternatively, or collectively, pillow 100 can include one or more other openings 140 for receiving one or more other inserts 142 therein via a portion of pillow 100 other than base 104 (e.g., in a side or the top of pillow 100). In at least one embodiment, one or more inserts 142 can be adapted for stiffening one or more neck supports 124, 128, 132, which can provide for an improved or increased ability to support the weight of a user's head and/or neck and/or to otherwise support stretching of a user's neck, whether separately or in combination with utilization of opening 136. In at least one embodiment, one or more inserts 142 can be adapted for stiffening one or more neck supports 124, 128, 132 by increasing the collective density of the neck support. In at least one embodiment, one or more inserts 142 can be adapted for stiffening one or more neck supports 124, 128, 132 by way of providing a stiffer or harder substrate than the remainder of the neck support (e.g., insert 142 can be made at least partially from plastic or another material and the remainder of a neck support can be made from foam). Insert 142 can be adapted to couple with body 102 or opening 140 in any manner according to an implementation of the disclosure, such as by friction fit or via the use of one or more fasteners (e.g., hook and loop material). One or more portions of pillow 100, such as body 102, insert 138 and insert 142 can be disposed in one or more covers (not shown), whether collectively or individually, such as removable or other covers made from cloth or another relatively soft material for at least partially protecting pillow 100 from contaminants such as moisture, dirt, etc.

As will be understood by a person of ordinary skill in the art having the benefits of the present disclosure, the exact size and shape of pillow 100 or any part or portion thereof (e.g., supports, support surfaces, openings, etc.) can vary from one implementation or embodiment to another depending on the particular goals or other relevant factors pertaining to such implementation or embodiment. For instance, one or more embodiments of pillow 100 can be sized and shaped for use or intended use by one or more classifications of, or otherwise designated types or groups of, people, such as groups differentiated by age, life stage (e.g., child, adolescent, adult), sex, or other variables, such as height or weight. As such, attributes of pillow 100 (or, e.g., a commercial embodiment thereof) such as dimensions, radiuses of curvature, stiffness, density, material type and other physical characteristics can be tailored as needed or desired for any actual or intended user or group of users. Any one or more of such variables can be chosen based on any information according to or relevant to an implementation or embodiment at hand, such as, for example, actual measurements of one or more persons or, as another example, average data or data ranges relating to any particular group or other designation of people of interest. Pillow 100 can be made from any material or materials according to an implementation of the disclosure, including, but not limited, foam, separately or in combination, in whole or in part. In at least one embodiment, which is but one of many, pillow 100 or a component thereof (e.g., one or more inserts 138, 142) can be made at least partially of closed cell cross-linked polyethylene foam. Other types of foam can also be suitable for one or more implementations of the disclosure, including, but not limited to, memory foam. Pillow 100 and its various components can be made from foam(s) of the same or different types, materials, and/or physical characteristics (e.g., density), separately or in combination, in whole or in part, as required or desired according to an implementation of the disclosure.

In at least one embodiment, a pillow can include a base, a front terminal end, a rear terminal end, a left side and a right side, a head support surface adapted to support at least a portion of a person's head, wherein at least a portion of the head support surface can be disposed at a head support height above the base, a first support having a first support surface with a first apex disposed at a first height above the base, a second support having a second support surface with a second apex disposed at a second height above the base, and a third support having a third support surface with a third apex disposed at a third height above the base.

In at least one embodiment, a first support surface can be disposed on the left side between the front and rear terminal ends and can be adapted to support at least a portion of a person's neck when the person can be lying supine with at least a portion of their neck in contact with the first support and at least a portion of their head in contact with the head support surface. A second support surface can be disposed on the right side between the front and rear terminal ends and can be adapted to support at least a portion of a person's neck when the person is lying supine with at least a portion of their neck in contact with the second support and at least a portion of their head in contact with the head support surface. A third support surface can be disposed frontward of the rear terminal end between the left and right sides and can be adapted to support at least a portion of a person's neck when the person is lying supine with at least a portion of their neck in contact with the third support and at least a portion of their head in contact with the head support surface. One or more heights, such as one or more of a first, second or third height can be greater than a head support height.

In at least one embodiment, one or more heights, which can include at least two of the first, second and third heights can be different. In at least one embodiment, each of the first, second and third heights are different. In at least one embodiment, a pillow can include a recess disposed between or otherwise relative to one or more surfaces or other components or portions of a pillow, such as a third or other support and a head support surface or portion thereof. In at least one embodiment, a pillow can include one or more openings, such as a partial or through opening, disposed between or otherwise relative to one or more surfaces or supports, such as at least partially between a third support and a head support surface. In at least one embodiment, a pillow can include one or more surfaces, such as a head support surface, which can include one or more grooves or other recesses or openings, such as a plurality of grooves, which can include one or more parallel or transverse grooves. In at least one embodiment, a plurality of grooves can be disposed between the front terminal end and the third support, separately or in combination, in whole or in part. In at least one embodiment, at least one of a plurality of grooves can be transverse to the front terminal end.

In at least one embodiment, a pillow can include one or more cavities in the base, such as one or more cavities that extend into at least one of the first, second and third supports, or into another portion of the pillow. One or more cavities can be adapted to receive at least a portion of an insert. A pillow can include one or more inserts, such as of the same or different sizes, shapes, materials, etc., which can include one or more inserts adapted to couple with one or more cavities.

In at least one embodiment, a pillow can include supports or support surfaces of one or more heights. In at least one embodiment, a first height can be less than a second height and a second height can be less than a third height. At least a portion of a third or other support surface can be disposed between or otherwise relative to a rear end or rear terminal end and at least one of first and second or other support surfaces.

A third support surface can intersect or otherwise cooperate with at least one of a first, second, or other support surface. At least a portion of one or more of the first, second and third support surfaces, or another surface, can be convex, concave, contoured, or otherwise shaped for supporting a person's body or portion thereof. In at least one embodiment, a pillow can include a transition or other surface(s) disposed at least partially between a head support surface and a front end or front terminal end.

In at least one embodiment, a pillow can include at least one of a recess and a through opening disposed between, in or otherwise relative to one or more supports or surfaces, such as a third support and a head support surface. A recess or opening can be adapted for receiving at least a portion of a person's head, which can include at least a portion of the crown of a person's head, such as, for example, when the person is lying supine or in another position, which can include lying on their side, such as with at least a portion of their neck in contact with one or more supports or support surfaces, such as the third or another support, and such as with at least a portion of their head in contact with, for example, the head support surface or a portion thereof, which in at least one embodiment can include at least a portion of a recess or opening.

In at least one embodiment, a pillow can include at least one of a recess and a through opening disposed between, in or otherwise relative to one or more supports or surfaces, such as a third support and a head support surface. A recess or opening can be adapted for receiving at least a portion of a person's head, which can include at least a portion of the crown of a person's head, such as, for example, when the person is lying supine or in another position, which can include lying on their side, such as with at least a portion of their neck in contact with one or more supports or support surfaces, such as any of the first and second supports, and, for example, at least a portion of their head in contact with a front side of the third support and at least a portion of their head in contact with at least a portion of the head support surface that is nearest, part of, or otherwise disposed relative to a recess or opening.

In at least one embodiment, a pillow can include one or more supports comprising one or more walls or other portions, such as inwardly or otherwise facing walls. One or more walls can be adapted for contacting one or more portions of a person, such as, for example, opposite sides of a person's head, such as when the person is lying supine or otherwise with at least a portion of their neck in contact with one or more supports, such as a third support, and at least a portion of their head in contact with a head support surface. In at least one embodiment, a pillow can include at least one of a recess and a through opening disposed at least partially between the third support and the head support surface, and one or more inserts configured to be at least partially disposed within the recess and/or through opening. One or more inserts can include one or more head support surfaces.

In at least one embodiment, a pillow can include a head support surface configured to support at least a portion of a person's head, a first support having a first support surface with a first apex disposed at a first height a second support having a second support surface with a second apex disposed at a second height, and a third support having a third support surface with a third apex disposed at a third height. One or more supports or support surfaces can support at least a portion of a person's neck when at least a portion of their head is in contact with a head support surface or a substrate surface, which can include being at least partially disposed in or through an opening. One or more of the heights can differ from one or more other heights. A pillow can include one or more openings and one or more inserts configured to be disposed therein. An insert can include one or more second or other head support surfaces.

In at least one embodiment, a pillow according to the disclosure can include a base, a front terminal end, a rear terminal end, a first side, a second side, a neck support and an opening for allowing at least a portion of a person's head to be disposed in or through the opening when the person is lying supine with at least a portion of the person's neck in contact with at least a portion of the neck support. In at least one embodiment, a pillow can have an opening configured for allowing at least a portion of a person's head to pass through the opening and pillow and into contact with a substrate surface beneath the pillow and/or person, such as a bed, table or floor. A pillow can but need not include one or more other neck supports disposed about the opening. A pillow can include a head support surface disposed next to the opening and/or the opening can be disposed in or through a head support portion of the pillow. One or more sides of a pillow can include a raised neck support in communication with an opening in or through the pillow. In at least one embodiment, a pillow according to the disclosure can include one neck support. In at least one embodiment, a pillow according to the disclosure can include more than one neck support. In at least one embodiment, a pillow according to the disclosure can be configured to support at least a portion of a person's neck and/or head while at least a portion of the person's head is supported by or on substrate surface under the pillow. In at least one embodiment, a pillow according to the disclosure can include a head support having a base, at least one opening in or through the head support, and at least one neck support disposed for supporting a person's neck when the person is lying on the pillow supine with a portion of their head disposed in or through the opening.

Other and further embodiments utilizing one or more aspects of the inventions described above can be devised without departing from the spirit of Applicant's disclosure. For example, pillow 100 can be or include any shape and/or any number of neck supports required or desired for a particular implementation of the disclosure. Further, the various methods and embodiments of the pillows can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the inventions has been described. Obvious modifications and alterations to the described embodiments are available to those of ordinary skill in the art having the benefits of the present disclosure. The disclosed and undisclosed embodiments are not intended to limit or restrict the scope or applicability of the inventions conceived of by the Applicant, but rather, in conformity with the patent laws, Applicant intends to fully protect all such modifications and improvements that come within the scope or range of equivalents of the following claims.

What is claimed is:

1. A pillow, comprising: a base, a front terminal end, a rear terminal end, a first side and a second side; a head support surface configured to support at least a portion of a person's head, wherein at least a portion of the head support surface is disposed at a head support height above the base; a first support having a first support surface with a first apex disposed at a first height above the base; a second support having a second support surface with a second apex disposed at a second height above the base; and a third support having a third support surface with a third apex disposed at a third height above the base; wherein the first support surface is disposed on the first side between the front and rear terminal ends and is configured to support at least a portion of a person's neck when the person is lying supine with at least a portion of the person's neck in contact with the first support and at least a portion of the person's head in contact with the head support surface; wherein the second support surface is disposed on the second side between the front and rear terminal ends and is configured to support at least a portion of the person's neck when the person is lying supine with at least a portion of the person's neck in contact with the second support and at least a portion of the person's head in contact with the head support surface; wherein the third support surface is disposed frontward of the rear terminal end between the first and second sides and is configured to support at least a portion of the person's neck when the person is lying supine with at least a portion of the person's neck in contact with the third support and at least a portion of the person's head in contact with the head support surface; and wherein the first, second and third heights are greater than the head support height; and wherein each of the first, second and third heights are different.

2. The pillow of claim 1, further comprising a recess disposed at least partially between the third support and the head support surface.

3. The pillow of claim 1, further comprising a through opening disposed at least partially between the third support and the head support surface, wherein the through opening is configured to allow at least a portion of the person's head to pass through the pillow and rest on a substrate surface beneath the pillow when the person is lying supine with at least a portion of the person's neck in contact with the third support.

4. The pillow of claim 1, wherein the head support surface further comprises a plurality of grooves.

5. The pillow of claim 4, wherein the plurality of grooves is disposed between the front terminal end and the third support.

6. The pillow of claim 5, wherein at least one of the plurality of grooves is transverse to the front terminal end.

7. The pillow of claim 1, further comprising a cavity in the base that extends into at least one of the first, second and third supports.

8. The pillow of claim 7, wherein the cavity is configured to receive at least a portion of an insert.

9. The pillow of claim 8, further comprising an insert configured to couple with the cavity.

10. The pillow of claim 1, wherein the first height is less than the second height and the second height is less than the third height.

11. The pillow of claim 1, wherein at least a portion of the third support surface is disposed between the rear terminal end and at least one of the first and second support surfaces.

12. The pillow of claim 1, wherein the third support surface intersects at least one of the first and second support surfaces.

13. The pillow of claim 1, wherein at least a portion of one or more of the first, second and third support surfaces is convex.

14. The pillow of claim 1, further comprising a transition surface disposed at least partially between the head support surface and the front terminal end.

15. The pillow of claim 1, further comprising at least one of a recess and a through opening disposed at least partially between the third support surface and the head support surface and configured to receive at least a portion of a crown of the person's head when the person is lying supine with at least a portion of the person's neck in contact with at least a portion of the third support surface.

16. The pillow of claim 1, further comprising at least one of a recess and a through opening disposed at least partially between the third support surface and the head support surface and configured to receive at least a portion of a crown of the person's head when the person is lying supine with at least a portion of the person's neck in contact with at least a portion of any of the first and second supports.

17. The pillow of claim 15, wherein the first and second supports comprise inwardly facing walls configured to contact opposite sides of the person's head when the person is lying supine with at least a portion of the person's neck in contact with the third support and at least a portion of the person's head disposed in the at least one recess or through opening.

18. The pillow of claim 1, further comprising at least one of a recess and a through opening disposed at least partially between the third support surface and the head support surface, and an insert configured to be at least partially disposed within the at least one recess or through opening, wherein the insert comprises a second head support surface.

19. A pillow, comprising:
a base, a front terminal end, a rear terminal end, a first side and a second side;
a head support surface configured to support at least a portion of a person's head, wherein the head support surface is disposed at a head support height above the base;
a first support having a first support surface with a first apex disposed at a first height above the base;
a second support having a second support surface with a second apex disposed at a second height above the base;
a third support having a third support surface with a third apex disposed at a third height above the base; and
a recess disposed between the third support and the head support surface, wherein the recess extends below the head support surface;
wherein the first support surface is disposed on the first side between the front and rear terminal ends and wherein the first apex runs along the first side;
wherein the second support surface is disposed on the second side between the front and rear terminal ends and wherein the second apex runs along the second side, parallel to the first side;
wherein the third support surface is disposed frontward of the rear terminal end between the first and second sides and wherein the third apex runs between the first and second sides;
wherein the first, second and third heights are greater than the head support height; and
wherein each of the first, second and third heights are different.

20. A pillow, comprising: a base, a front terminal end, a rear terminal end, a first side and a second side; a head support surface configured to support at least a portion of a person's head, wherein the head support surface is disposed at a head support height above the base; a first support having a first support surface with a first apex disposed at a first height above the base; a second support having a second support surface with a second apex disposed at a second height above the base; a third support having a third support surface with a third apex disposed at a third height above the base; and a through opening disposed between the third support surface and the head support surface, wherein the through opening extends from the head support surface to the base; wherein the first support surface is disposed on the first side between the front and rear terminal ends; wherein the second support surface is disposed on the second side between the front and rear terminal ends; wherein the third support surface is disposed frontward of the rear terminal end between the first and second sides; and wherein the first, second and third heights are greater than the head support height; and wherein each of the first, second and third heights are different.

* * * * *